United States Patent
Goetz et al.

(10) Patent No.: US 7,919,619 B2
(45) Date of Patent: Apr. 5, 2011

(54) HETEROCYCLICAL, SUBSTITUTED PHENAZINAMINE-TYPE NON-LINEAR OPTIC CHROMOPHORE ARCHITECTURES

(76) Inventors: Frederick J. Goetz, Wilmington, DE (US); Frederick J. Goetz, Jr., Wilmington, DE (US)

( * ) Notice: Subject to any disclaimer, the term of this patent is extended or adjusted under 35 U.S.C. 154(b) by 0 days.

(21) Appl. No.: 11/666,320

(22) PCT Filed: Oct. 26, 2005

(86) PCT No.: PCT/US2005/039010
§ 371 (c)(1),
(2), (4) Date: Feb. 8, 2008

(87) PCT Pub. No.: WO2006/050128
PCT Pub. Date: May 11, 2006

(65) Prior Publication Data
US 2008/0139812 A1 Jun. 12, 2008

Related U.S. Application Data

(60) Provisional application No. 60/623,204, filed on Oct. 29, 2004.

(51) Int. Cl.
*C07D 241/46* (2006.01)
(52) U.S. Cl. .................................................. 544/348
(58) Field of Classification Search ............... 544/348
See application file for complete search history.

(56) References Cited

U.S. PATENT DOCUMENTS

| | | | |
|---|---|---|---|
| 5,679,763 | A | 10/1997 | Jen et al. |
| 6,067,186 | A | 5/2000 | Dalton et al. |
| 2007/0260062 | A1 | 11/2007 | Goetz et al. |
| 2007/0260063 | A1 | 11/2007 | Goetz et al. |
| 2008/0009620 | A1 | 1/2008 | Goetz et al. |
| 2009/0005561 | A1 | 1/2009 | Goetz et al. |

FOREIGN PATENT DOCUMENTS
WO WO-00/09613 A2 2/2000

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Chem. Abstr., vol. 23, No. 16, 1929, pp. 3914-3916, abstract No. 2966.
Lukes, V., et al., "Non-Linear Optical Properties of new Bridged Bis-Thienyls I. Pyrazine-Based Bridges: Theory, Synthesis and Spectra", Elsevier Science, 2001. vol. 124, pp. 279-286.
Raghukumar, V., et al., Synthesis of Nicotinonitrile Derivatives as a New Class of NLO Materials, Tetrahedron, 2003, vol. 59, pp. 3761-3768.
Imai, K., et al., "Synthesis and Properties of Thermally Stable Ladder Polymers Containing the 1,4-Pyrazine Ring Obtained from Polyheterocyclization of Tetramines and Tetraketones in Poly(phosphoric acid) and m-Cresol", Macromolecules, 1973, vol. 6, No. 2, pp. 158-162.
Qin, A., et al., "Design and Synthesis of a Thermally Stable Second-Order Nonlinear Optical Chromophore and Its Poled Polymers", Journal of Polymer Science: Part A: A Polymer Chemistry, 2003, vol. 41, pp. 2846-2853.
Cotlet, M. et al., Intramolecular Directional Forster Resonance Energy Transfer at the Single Molecule Level in a Dendritic System., J. Am. Chem. Soc., 2003, vol. 125, pp. 13609-13617.
Mikroyannidis, J.A. et al., "Synthesis by the Gilch Method of Blue-Light-Emitting Poly(p-phenylenevinylene) Derivatives Bearing Highly Phenylate Pendants", Chem. Mater., 2003, vol. 15, pp. 1865-1871.
Mongin, O. et al., "Synthesis and Two-Photon Absorption of Triphenylbenzene-Cored Dendritic Chromophores", Tetrahedron Letters, 2003, vol. 44, pp. 2813-2816.
Spiliopoulos, I. K. et al., "Synthesis of Methacrylic Monomers Bearing Stilbenoid Chromophore and Their Free-Radical Polymerization to Give Luminescent Polymers", Macromolecules, 2002, vol. 35, pp. 7254-7261.
Spiliopoulos, I. K. et al., "Synthesis of Poly(p-phenylene vinylene)- and Poly(phenylene ethynylene)-Based Polymers Containing p-Terphenyl in the Main Chain with Alkoxyphenyl Side Groups", Journal of Polymer Science: Part A: Polymer Chemistry, 2002, vol. 40, pp. 2591-2600.
Maus, M. et al., "Intramolecular Energy Hopping and Energy Trapping in Polyphenylene Dendrimers with Multiple Peryleneimide Donor Chromophores and a Terryleneimide Acceptor Trap Chromophore", J. Am. Chem. Soc., 2001, vol. 123, pp. 7668-7676.
Bonvoisin, J. et al., "Organic Mixed Valence Systems. II. Two-Centers and Three-Centers Compounds with Meta Connections around a Central Phenylene Ring", J. Phys. Chem., 1996, vol. 100, pp. 17079-07082.

* cited by examiner

*Primary Examiner* — James O Wilson
*Assistant Examiner* — Douglas M Willis
(74) *Attorney, Agent, or Firm* — Connolly Bove Lodge & Hutz LLP

(57) ABSTRACT

NLO chromophores of the following general formula:

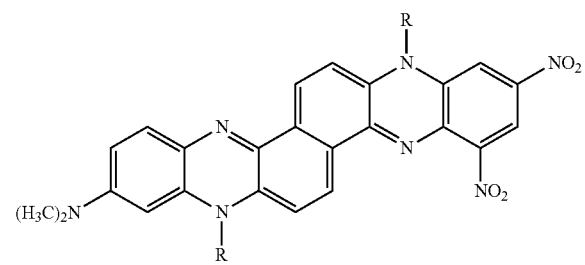

wherein each R represents a spacer system or substituent moiety as disclosed herein.

7 Claims, No Drawings

HETEROCYCLICAL, SUBSTITUTED PHENAZINAMINE-TYPE NON-LINEAR OPTIC CHROMOPHORE ARCHITECTURES

BACKGROUND OF THE INVENTION

Polymeric electro-optic (EO) materials have demonstrated enormous potential for core application in a broad range of systems and devices, including phased array radar, satellite and fiber telecommunications, cable television (CATV), optical gyroscopes for application in aerial and missile guidance, electronic counter measure systems (ECM) systems, backplane interconnects for high-speed computation, ultrafast analog-to-digital conversion, land mine detection, radio frequency photonics, spatial light modulation and all-optical (light-switching-light) signal processing.

Nonlinear optic materials are capable of varying their first-, second-, third- and higher-order polarizabilities in the presence of an externally applied electric field or incident light (two-photon absorption). In telecommunication applications, the second-order polarizability (hyperpolarizability or $\beta$) and third-order polarizability (second-order hyperpolarizability or $\gamma$) are currently of great interest. The hyperpolarizability is related to the change of a NLO material's refractive index in response to application of an electric field. The second-order hyperpolarizability is related to the change of refractive index in response to photonic absorbance and thus is relevant to all-optical signal processing. A more complete discussion of nonlinear optical materials may be found in D. S. Chemla and J. Zyss, Nonlinear optical properties of organic molecules and crystals, Academic Press, 1987 and K.-S. Lee, Polymers for Photonics Applications I, Springer 2002.

Many NLO molecules (chromophores) have been synthesized that exhibit high molecular electro-optic properties. The product of the molecular dipole moment ($\mu$) and hyperpolarizability ($\beta$) is often used as a measure of molecular electro-optic performance due to the dipole's involvement in material processing. One chromophore originally evaluated for its extraordinary NLO properties by Bell Labs in the 1960s, Disperse Red (DR), exhibits an electro-optic coefficient $\mu\beta \sim 580 \times 10^{-48}$ esu. Current molecular designs, including FTC, CLD and GLD, exhibit $\mu\beta$ values in excess of $10,000 \times 10^{-48}$ esu. See Dalton et al., "New Class of High Hyperpolarizability Organic Chromophores and Process for Synthesizing the Same", WO 00/09613.

Nevertheless extreme difficulties have been encountered translating microscopic molecular hyperpolarizabilities ($\beta$) into macroscopic material hyperpolarizabilities ($X^{(2)}$). Molecular subcomponents (chromophores) must be integrated into NLO materials that exhibit: (i) a high degree of macroscopic nonlinearity; and, (ii) sufficient temporal, thermal, chemical and photochemical stability. Simultaneous solution of these dual issues is regarded as the final impediment in the broad commercialization of EO polymers in numerous government and commercial devices and systems.

The production of high material hyperpolarizabilities ($X^{(2)}$) is limited by the poor social character of NLO chromophores. Commercially viable materials must incorporate chromophores with the requisite molecular moment statistically oriented along a single material axis. In order to achieve such an organization, the charge transfer (dipolar) character of NLO chromophores is commonly exploited through the application of an external electric field during material processing which creates a localized lower-energy condition favoring noncentrosymmetric order. Unfortunately, at even moderate chromophore densities, molecules form multi-molecular dipolarly-bound (tentrosymmetric) aggregates that cannot be dismantled via realistic field energies. As a result, NLO material performance tends to decrease dramatically after approximately 20-30% weight loading. One possible solution to this situation is the production of higher performance chromophores that can produce the desired hyperpolar character at significantly lower molar concentrations.

Attempts at fabricating higher performance NLO chromophores have largely failed due to the nature of the molecular architecture employed throughout the scientific community. Currently all high-performance chromophores (e.g., CLD, FTC, GLD, etc.) incorporate protracted "naked" chains of alternating single-double $\pi$-conjugated covalent bonds. Researchers such as Dr. Seth Marder have provided profound and detailed studies regarding the quantum mechanical function of such "bond-alternating" systems which have been invaluable to our current understanding of the origins of the NLO phenomenon and have in turn guided present-day chemical engineering efforts. Although increasing the length of these chains generally improves NLO character, once these chains exceed ~2 nm, little or no improvement in material performance has been recorded. Presumably this is largely due to: (i) bending and rotation of the conjugated atomic chains which disrupts the $\pi$-conduction of the system and thus reduces the resultant NLO character; and, (ii) the inability of such large molecular systems to orient within the material matrix during poling processes due to environmental steric inhibition. Thus, future chromophore architectures must exhibit two important characteristic: (i) a high degree of rigidity, and (ii) smaller conjugative systems that concentrate NLO activity within more compact molecular dimensions.

Long-term thermal, chemical and photochemical stability is the single most important issues in the construction of effective NLO materials. Material instability is in large part the result of three factors: (i) the increased susceptibility to nucleophilic attack of NLO chromophores due to molecular and/or intramolecular (CT) charge transfer or (quasi)-polarization, either due to high-field poling processes or photonic absorption at molecular and intramolecular resonant energies; (ii) molecular motion due to photo-induced cis-trans isomerization which aids in the reorientation of molecules into performance-detrimental centrosymmetric configurations over time; and (iii) the extreme difficulty in incorporating NLO chromophores into a holistic cross-linked polymer matrix due to inherent reactivity of naked alternating-bond chromophore architectures. Thus, future chromophore architectures: (i) must exhibit improved CT and/or quasi-polar state stability; (ii) must not incorporate structures that undergo photo-induced cis-trans isomerization; and (iii) must be highly resistant to polymerization processes through the possible full-exclusion of naked alternating bonds.

The present invention seeks to fulfill these needs through the innovation of fully heterocyclical anti-aromatic chromophore design. The heterocyclical systems described herein do not incorporate naked bond-alternating chains that are susceptible to bending or rotation. The central anti-aromatic conductor "pull" the molecule into a quasi-CT state; since aromaticity and non-CT states are both favorably low-energy conditions, charge transfer and aromaticity within the molecular systems described herein are set against each other within a competitive theater. This competitive situation is known as CAPP engineering or Charge-Aromaticity Push-Pull. As a result, the incorporation of anti-aromatic systems dramatically improves the conductive properties of the central $\pi$-conjugated bridge providing for smaller molecular lengths with significantly greater NLO property. Because all the systems described, herein are aromatic in their CT state and quasi-aromatic in their intermediate quasi-polarized states, this structure is expected to dramatically improve polar-state stability. Furthermore, novel electronic acceptor systems are described herein which are expected to significantly improve excited-state and quasi-CT delocalization making the overall systems less susceptible to nucleophilic attack. The heterocyclical nature of all the systems described herein forbids the existence of photo-induced cis-trans isomerization which is suspected as a cause of both material and molecular degeneration. Finally, the invention provides for chromophoric systems that are devoid of naked alternating bonds that are reactive to polymerization conditions.

SUMMARY OF THE INVENTION

The present invention relates to NLO chromophores for the production of first-, second-, third- and/or higher order polarizabilities of the form of Formula I:

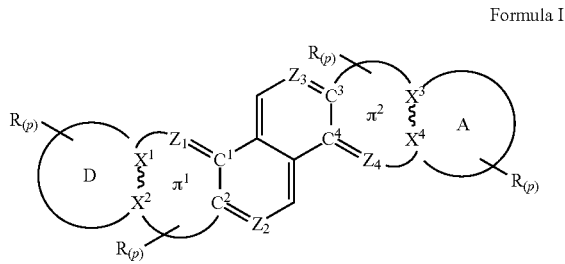

Formula I or an acceptable salt thereof; wherein (p) is 0-6;

∿ are independently at each occurrence a covalent chemical bond;

$X^{1-4}$ are independently selected from C, N, O or S;

$Z^{1-4}$ are independently N, CH or CR; where R is defined below.

D is an organic electron donating group having equal or lower electron affinity relative to the electron affinity of A. In the presence of $\pi^1$, D is attached to the remainder of the molecule at two atomic positions $X^1$ and $X^2$. In the absence of $\pi^1$, D is attached to the remainder of the molecule at two atomic positions $Z^1$ and $C^2$.

A is an organic electron accepting group having equal or higher electron affinity relative to the electron affinity of D. In the presence of $\pi^2$, A is attached to the remainder of the molecule at two atomic positions $X^3$ and $X^4$. In the absence of $\pi^2$, A is attached to the remainder of the molecule at two atomic positions $Z^4$ and $C^3$.

π1 comprises $X^1$ and $X^2$ and is absent or a bridge joining atomic pairs $Z^1$ and $C^2$ to $X^1$ ∿$X^2$ and which provides electronic conjugation between D and an anti-aromatic system comprising $C^1$, $C^2$, $C^3$, $C^4$, $Z^1$, $Z^2$, $Z^3$ and $Z^4$.

$\pi^2$ comprises $X^3$ and $X^4$ and is absent or a bridge joining atomic pairs $C^3$ and $Z^4$ to $X^3$ ∿$X^4$ and which provides electronic conjugation between A and said anti-aromatic system.

R is independently selected from:

(i) a spacer system of the Formula II

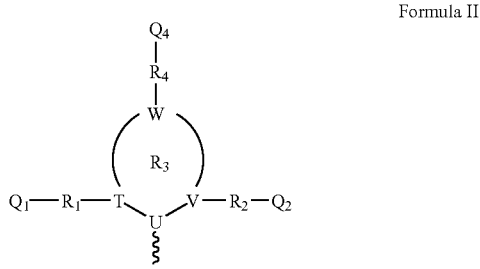

Formula II or an acceptable salt thereof; wherein $R_3$ is a $C_6$-$C_{10}$ aryl, $C_6$-$C_{10}$ heteroaryl, 4-10 membered heterocyclic or a $C_6$-$C_{10}$ saturated cyclic group; 1 or 2 carbon atoms in the foregoing cyclic moieties are optionally substituted by an oxo (=O) moiety; and the foregoing R3 groups are optionally substituted by 1 to 3 $R_5$ groups;

$R_1$ and $R_2$ are independently selected from the list of substituents provided in the definition of $R_3$, $(CH_2)_t(C_6$-$C_{10}$ aryl) or $(CH_2)_t$(4-10 membered heterocyclic), t is an integer ranging from 0 to 5, and the foregoing $R_1$ and $R_2$ groups are optionally substituted by 1 to 3 $R^5$ groups;

$R_4$ is independently selected from the list of substituents provided in the definition of $R_3$, a chemical bond (—), or hydrogen;

each $Q^1$, $Q^2$, and $Q^4$ is independently selected from hydrogen, halo, $C_1$-$C_{10}$ alkyl, $C_2$-$C_{10}$ alkenyl, $C_2$-$C_{10}$ alkynyl, nitro, trifluoromethyl, trifluoromethoxy, azido, —$OR^5$, —$NR^6C(O)OR^5$, —$NR^6SO_2R^5$, —$SO_2NR^5R^6$, —$NR^6C(O)R^5$, —$C(O)NR^5R^6$, —$NR^5R^6$, —$S(O)_jR^7$ wherein j is an integer ranging from 0 to 2, —$NR^5(CR^6R^7)_tOR^6$, —$(CH_2)_t(C_6$-$C_{10}$ aryl), —$SO_2(CH_2)_t(C_6$-$C_{10}$ aryl), —$S(CH_2)_t(C_6$-$C_{10}$ aryl), —$O(CH_2)_t(C_6$-$C_{10}$ aryl), —$(CH_2)_t$(4-10 membered heterocyclic), and —$(CR^6R^7)_mOR^6$, wherein m is an integer from 1 to 5 and t is an integer from 0 to 5; with the proviso that when $R^4$ is hydrogen $Q^4$ is not available; said alkyl group optionally contains 1 or 2 hetero moieties selected from O, S and —N($R^6$)— said aryl and heterocyclic Q groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (=O) moiety; and the alkyl, aryl and heterocyclic moieties of the foregoing Q groups are optionally substituted by 1 to 3 substituents independently selected from nitro, trifluoromethyl, trifluoromethoxy, azido, —$NR^6SO_2R^5$, —$SO_2NR^5R^6$, —$NR^6C(O)R^5$, —$C(O)NR^5R^6$, —$NR^5R^6$, —$(CR^6R^7)_mOR^6$ wherein m is an integer from 1 to 5, —$OR^5$ and the substituents listed in the definition of $R^5$;

each $R^5$ is independently selected from H, $C_1$-$C_{10}$ alkyl, —$(CH_2)_t(C_6$-$C_{10}$ aryl), and —$(CH_2)_t$(4-10 membered heterocyclic), wherein t is an integer from 0 to 5; said alkyl group optionally includes 1 or 2 hetero moieties selected from O, S and —N($R^6$)— said aryl and heterocyclic $R^5$ groups are optionally fused to a $C_6$-$C_{10}$ aryl group, a $C_5$-$C_8$ saturated cyclic group, or a 4-10 membered heterocyclic group; and the foregoing $R^5$ substituents, except H, are optionally substituted by 1 to 3 substituents independently selected from nitro, trifluoromethyl, trifluoromethoxy, azido, —$NR^6C(O)R^7$, —$C(O)NR^6R^7$, —$NR^6R^7$, hydroxy, $C_1$-$C_6$ alkyl, and $C_1$-$C_6$ alkoxy;

each $R^6$ and $R^7$ is independently H or $C_1$-$C_6$ alkyl;

T, U and V are each independently selected from C (carbon), O (oxygen), N (nitrogen), and S (sulfur), and are included within $R^3$;

T, U, and V are immediately adjacent to one another; and W is any non-hydrogen atom in $R^3$ that is not T, U, or V; or (ii) hydrogen, halo, $C_1$-$C_{10}$ alkyl, $C_2$-$C_{10}$ alkenyl, $C_2$-$C_{10}$ alkynyl, nitro, trifluoromethyl, trifluoromethoxy, azido, —$OR^5$, —$NR^6C(O)OR^5$, —$NR^6SO_2R^5$, —$SO_2NR^5R^6$, —$NR^6C(O)R^5$, —$C(O)NR^5R^6$, —$NR^5R^6$, —$S(O)_jR^7$ wherein j is an integer ranging from 0 to 2, —$NR^5(CR^6R^7)_t$ $OR^6$, —$(CH_2)_t(C_6$-$C_{10}$ aryl, —$SO_2(CH_2)_t(C_6$-$C_{10}$ aryl), —$S(CH_2)_t(C_6$-$C_{10}$ aryl), —$O(CH_2)_t(C_6$-$C_{10}$ aryl), —$(CH_2)_t$(4-10 membered heterocyclic), and —$(CR^6R^7)_mOR^6_1$ wherein m is an integer from 1 to 5 and t is an integer from 0 to 5; said alkyl group optionally contains 1 or 2 hetero moieties selected from O, S and —N($R^6$)—, wherein $R^5$, $R^6$ and $R^7$ are as defined above.

Another embodiment of the present invention refers to the compounds of Formula I wherein the $\pi^1$ conjugative bridge and $C^2$ and $Z^1$ of the anti-aromatic system are connected in a manner selected from the group consisting of:

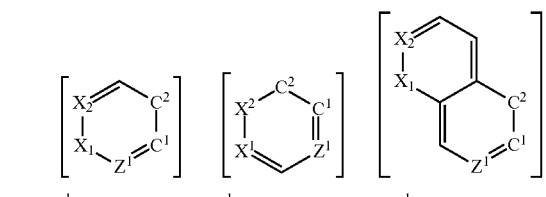

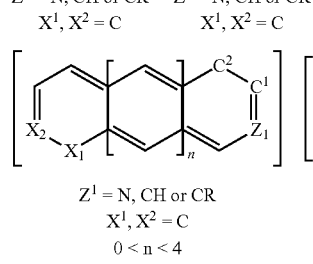

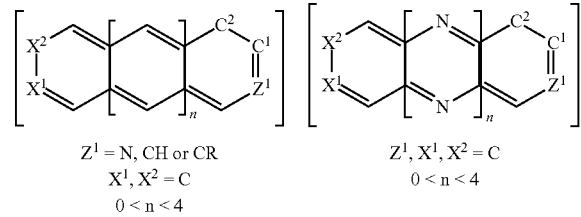

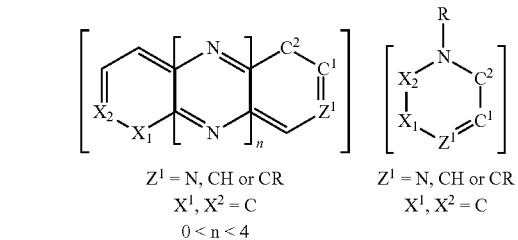

Wherein R is as defined above.

Another embodiment of the present invention refers to the compounds of Formula I wherein the electron donating group (D) and $X^1$ and $X^2$ of the $\pi^1$ conjugative bridge are connected in a manner selected from the group consisting of:

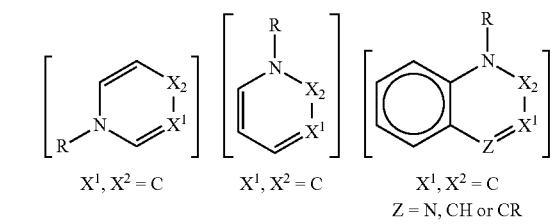

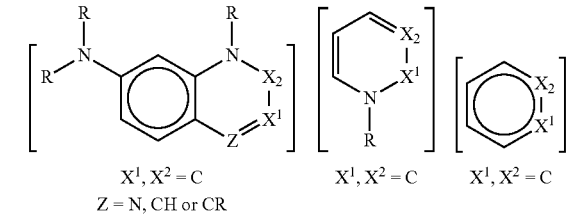

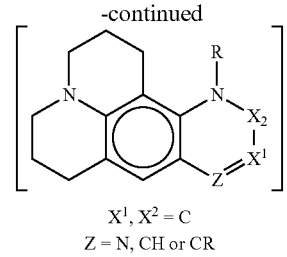

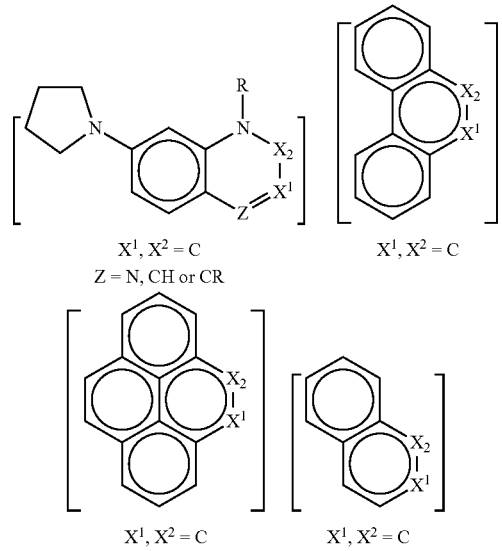

And wherein R is as defined above.

Another embodiment of the present invention refers to the compounds of Formula I wherein the $\pi^2$ conjugative bridge and $C^3$ and $Z^4$ of the anti-aromatic system are connected in a manner selected from the group consisting of:

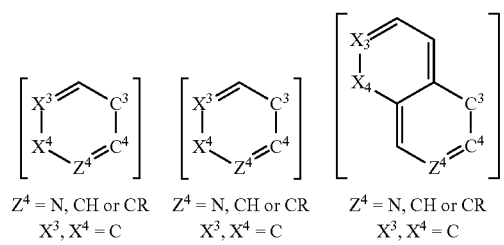

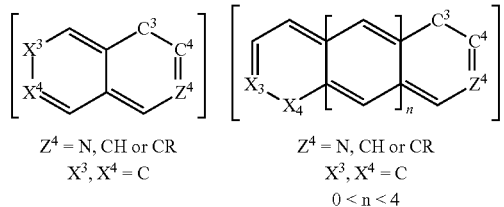

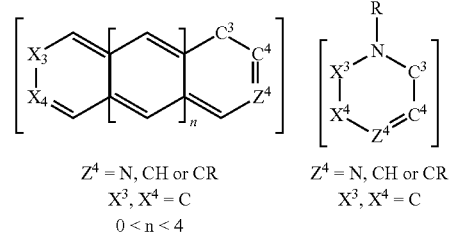

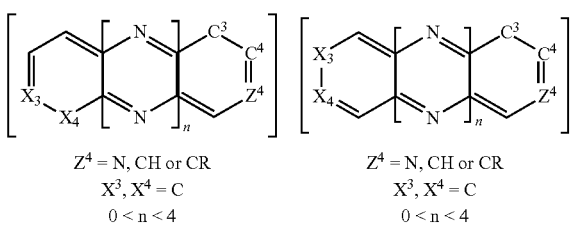

Z⁴ = N, CH or CR
X³, X⁴ = C
0 < n < 4

Z⁴ = N, CH or CR
X³, X⁴ = C
0 < n < 4

Wherein R is as defined above.

Another embodiment of the present invention refers to the compounds of Formula I wherein the electron accepting group (A) and $X^3$ and $X^4$ of the $\pi^2$ conjugative bridge are connected in a manner selected from the group consisting of;

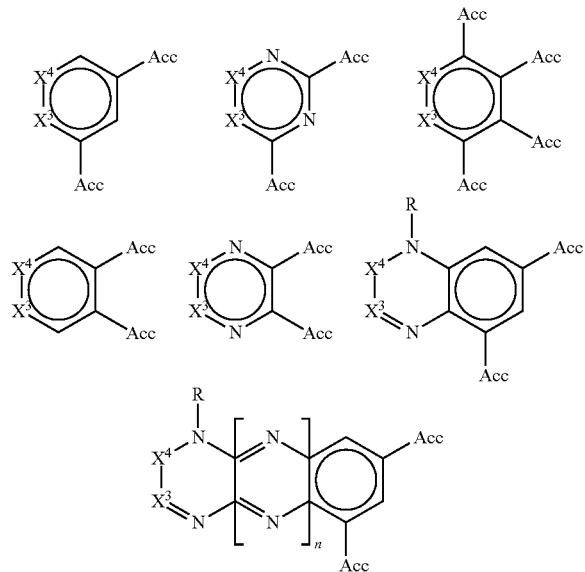

wherein R is defined above independently at each occurrence; and, Acc is an electron accepting group selected from CN, $NO_2$, $SO_2R$ and 0<n<5.

Another nonlimiting example of the invention includes the following chromophore:

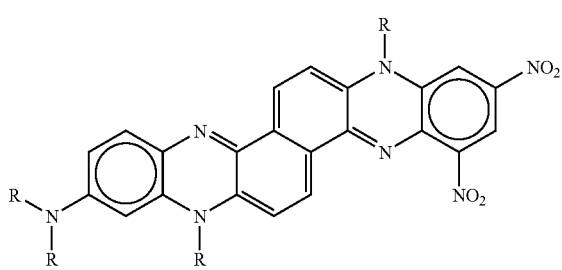

wherein R is defined above, independently at each occurrence.

Another nonlimiting example of the invention includes the following chromophore:

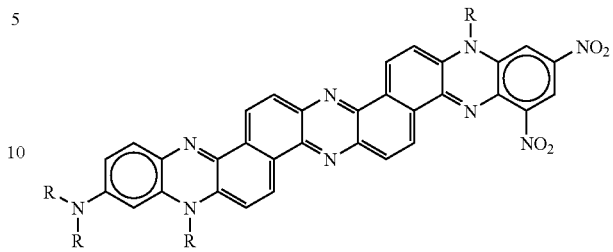

wherein R is defined above, independently at each occurrence.

In this invention the term "nonlinear optic chromophore" (NLOC) is defined as molecules or portions of a molecule that create a nonlinear optic effect when irradiated with light. The chromophores are any molecular unit whose interaction with light gives rise to the nonlinear optical effect. The desired effect may occur at resonant or nonresonant wavelengths. The activity of a specific chromophore in a nonlinear optic material is stated as their hyper-polarizability, which is directly related to the molecular dipole moment of the chromophore.

In this invention, the term "halo," unless otherwise indicated, includes fluoro, chloro, bromo or iodo. Preferred halo groups are fluoro, chloro and bromo.

The term "alkyl," as used herein, unless otherwise indicated, includes saturated monovalent hydrocarbon radicals having straight, cyclic or branched moieties. It is understood that for cyclic moieties at least three carbon atoms are required in said alkyl group.

The term "alkenyl," as used herein, unless otherwise indicated, includes monovalent hydrocarbon radicals having at least one carbon-carbon double bond and also having straight, cyclic or branched moieties as provided above in the definition of "alkyl."

The term "alkynyl," as used herein, unless otherwise indicated, includes monovalent hydrocarbon radicals having at least one carbon-carbon triple bond and also having straight, cyclic or branched moieties as provided above in the definition of "alkyl."

The term "alkoxy," as used herein, unless otherwise indicated, includes O-alkyl groups wherein "alkyl" is as defined above.

The term "aryl," as used herein, unless otherwise indicated, includes an organic radical derived from an aromatic hydrocarbon by removal of one hydrogen, such as phenyl or naphthyl.

The term "heteroaryl," as used herein, unless otherwise indicated, includes an organic radical derived by removal of one hydrogen atom from a carbon atom in the ring of a heteroaromatic hydrocarbon, containing one or more heteroatoms independently selected from O, S, and N. Heteroaryl groups must have at least 5 atoms in their ring system and are optionally substituted independently with 0-2 halogen, trifluoromethyl, $C_1$-$C_6$ alkoxy, $C_1$-$C_6$ alkyl, or nitro groups.

The term "4-10 membered heterocyclic," as used herein, unless otherwise indicated, includes aromatic and non-aromatic heterocyclic groups containing one or more heteroatoms each selected from O, S and N, wherein each heterocyclic group has from 4-10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, $^3$H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The term "saturated cyclic group" as used herein, unless otherwise indicated, includes non-aromatic, fully saturated cyclic moieties wherein alkyl is as defined above.

The phrase "acceptable salt(s)", as used herein, unless otherwise indicated, includes salts of acidic or basic groups which may be present in the compounds of the invention. The compounds of the invention that are basic in nature are capable of forming a wide variety of salts with various inorganic and organic acids. The acids that may be used to prepare pharmaceutically acceptable acid addition salts of such basic compounds of the invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the invention that are acidic in nature are capable of forming base salts with various pharmacologically acceptable cations. Examples of such salts include the alkali metal or alkaline earth metal salts and particularly the sodium and potassium salts.

The term "solvate," as used herein includes a compound of the invention or a salt thereof, that further includes a stoichiometric or non-stoichiometric amount of a solvent bound by non-covalent intermolecular forces.

The term "hydrate," as used herein refers to a compound of the invention or a salt thereof, that further includes a stoichiometric or non-stoichiometric amount of water bound by non-covalent intermolecular forces.

Certain compounds of the present invention may have asymmetric centers and therefore appear in different enantiomeric forms. This invention relates to the use of all optical isomers and stereoisomers of the compounds of the invention and mixtures thereof. The compounds of the invention may also appear as tautomers. This invention relates to the use of all such tautomers and mixtures thereof.

The subject invention also includes isotopically-labelled compounds, and the commercially acceptable salts thereof, which are identical to those recited in Formulas I and II but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Compounds of the present invention and commercially acceptable salts of said compounds which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain advantages resulting from greater stability. Isotopically labelled compounds of Formula I of this invention can generally be prepared by carrying out the procedures disclosed in the Schemes and/or in the Examples and Preparations below, by substituting a readily available isotopically labelled reagent for a non-isotopically labelled reagent.

Each of the patents, patent applications, published International applications, and scientific publications referred to in this patent application is incorporated herein by reference in its entirety.

DETAILED DESCRIPTION OF THE INVENTION

The compounds of Formula I are useful structures for the production of NLO effects.

The first-order hyperpolarizability ($\beta$) is one of the most common and useful NLO properties. Higher-order hyperpolarizabilities are useful in other applications such as all-optical (light-switching-light) applications. To determine if a material, such as a compound or polymer, includes a nonlinear optic chromophore with first-order hyperpolar character, the following test may be performed. First, the material in the form of a thin film is placed in an electric field to align the dipoles. This may be performed by sandwiching a film of the material between electrodes, such as indium tin oxide (ITO) substrates, gold films, or silver films, for example.

To generate a poling electric field, an electric potential is then applied to the electrodes while the material is heated to near its glass transition ($T_g$) temperature. After a suitable period of time, the temperature is gradually lowered while maintaining the poling electric field. Alternatively, the material can be poled by corona poling method, where an electrically charged needle at a suitable distance from the material film provides the poling electric field. In either instance, the dipoles in the material tend to align with the field.

The nonlinear optical property of the poled material is then tested as follows. Polarized light, often from a laser, is passed through the poled material, then through a polarizing filter, and to a light intensity detector. If the intensity of light received at the detector changes as the electric potential applied to the electrodes is varied, the material incorporates a nonlinear optic chromophore and has an electro-optically variable refractive index. A more detailed discussion of techniques to measure the electro-optic constants of a poled film that incorporates nonlinear optic chromophores may be found in Chia-Chi Teng, Measuring Electro-Optic Constants of a Poled Film, in Nonlinear Optics of Organic Molecules and Polymers, Chp. 7, 447-49 (Hari Singh Nalwa & Seizo Miyata eds., 1997), incorporated by reference in its entirety, except that in the event of any inconsistent disclosure or definition from the present application, the disclosure or definition herein shall be deemed to prevail.

The relationship between the change in applied electric potential versus the change in the refractive index of the material may be represented as its EO coefficient $r_{33}$. This effect is commonly referred to as an electro-optic, or EO, effect. Devices that include materials that change their refractive index in response to changes in an applied electric potential are called electro-optical (EO) devices.

An example compound of the Formula I may be prepared according to the following reaction scheme. R, in the reaction scheme and discussion that follow, is as defined above.

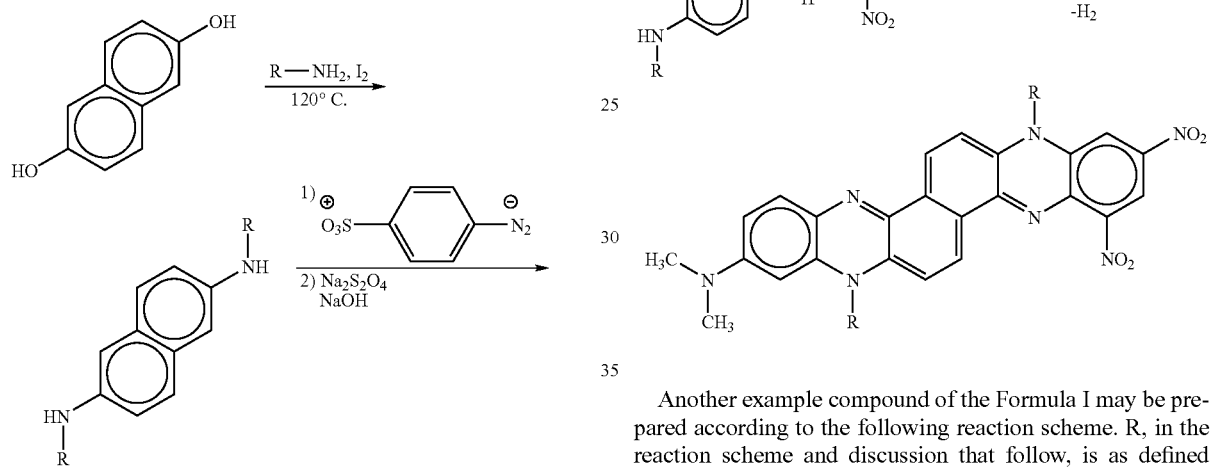

Another example compound of the Formula I may be prepared according to the following reaction scheme. R, in the reaction scheme and discussion that follow, is as defined above.

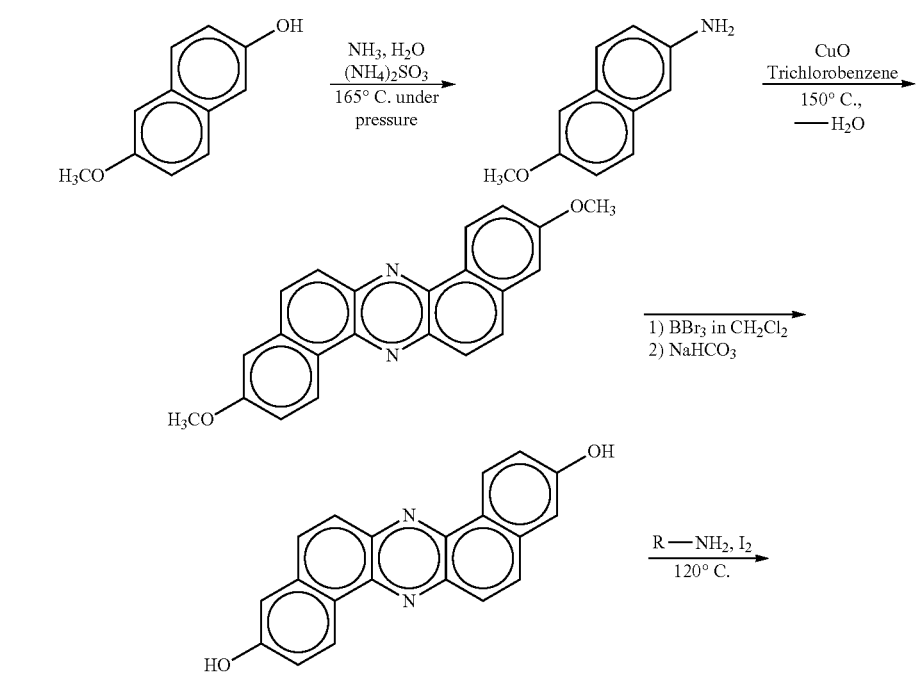

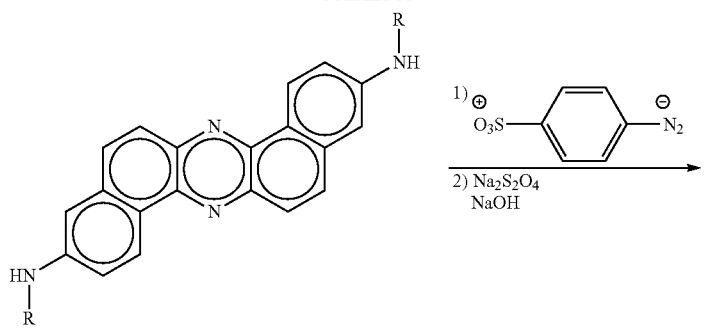
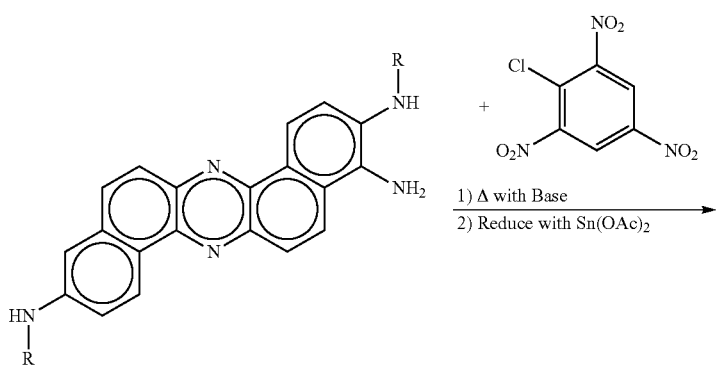
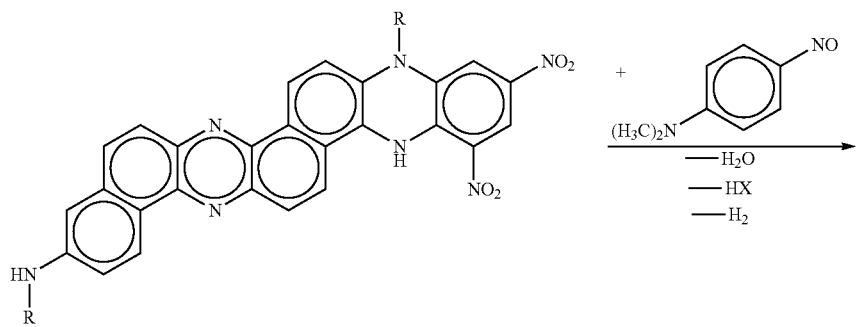
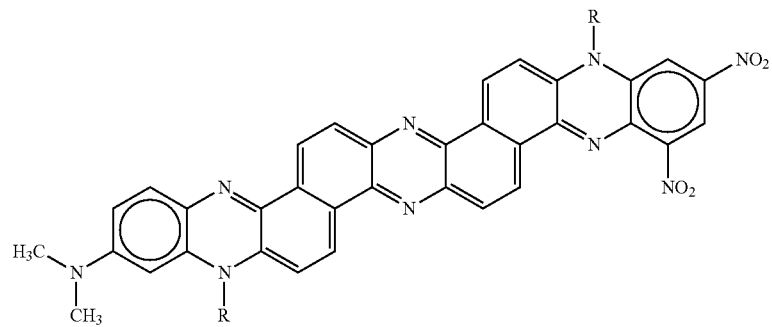

We claim:
1. A compound of the formula:

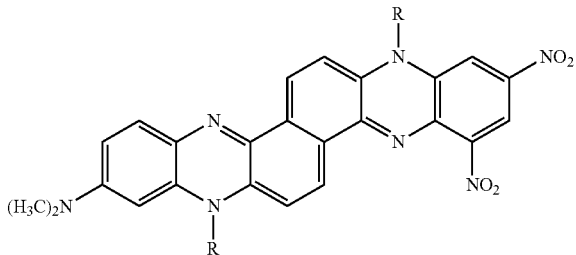

wherein each R is independently selected from:
(i) a spacer system of the Formula II

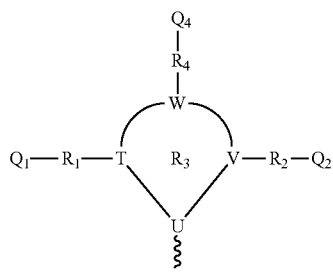

Formula II or a commercially acceptable salt thereof; wherein
$R_3$ is a $C_6$-$C_{10}$ aryl, $C_6$-$C_{10}$ heteroaryl, 4-10 membered heterocyclic or a $C_6$-$C_{10}$ saturated cyclic group; 1 or 2 carbon atoms in the foregoing cyclic moieties are optionally substituted by an oxo (=O) moiety; and the foregoing $R^3$ groups are optionally substituted by 1 to 3 $R^5$ groups;
$R_1$ and $R_2$ are independently selected from the list of substituents provided in the definition of $R_3$, $(CH_2)_t(C_6\text{-}C_{10}$ aryl) or $(CH_2)_t$(4-10 membered heterocyclic), t is an integer ranging from 0 to 5, and the foregoing $R_1$ and $R_2$ groups are optionally substituted by 1 to 3 $R^5$ groups;
$R_4$ is independently selected from the list of substituents provided in the definition of $R_3$, a chemical bond (—), or hydrogen;
each $Q^1$, $Q^2$, and $Q^4$ is independently selected from hydrogen, halo, $C_1$-$C_{10}$ alkyl, $C_2$-$C_{10}$ alkenyl, $C_2$-$C_{10}$ alkynyl, nitro, trifluoromethyl, trifluoromethoxy, azido, —$OR^5$, 13 $NR^6C(O)OR^5$, —$NR^6SO_2R^5$, —$SO_2NR^5R^6$, —$NR^6C(O)R^5$, —$C(O)NR^5R^6$, —$S(O)_jR^7$ wherein j is an integer ranging from 0 to 2, —$NR^5(CR^6R^7)_tOR^6$, —$(CH_2)_t(C_6\text{-}C_{10}$aryl), —$SO_2(CH_2)_t(C_6\text{-}C_{10}$ aryl), —$S(CH_2)_t(C_6\text{-}C_{10}$ aryl), —$O(CH_2)_t(C_6\text{-}C_{10}$ aryl), —$(CH_2)_t$(4-10 membered heterocyclic), and —$(CR^6R^7)_m$ $OR^6$, wherein m is an integer from 1 to 5 and t is an integer from 0 to 5; with the proviso that when $R^4$ is hydrogen $Q^4$ is not available; said alkyl group optionally contains 1 or 2 hetero moieties selected from O, S and —$N(R^6)$— said aryl and heterocyclic Q groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (=O) moiety; and the alkyl, aryl and heterocyclic moieties of the foregoing Q groups are optionally substituted by 1 to 3 substituents independently selected from nitro, trifluoromethyl, trifluoromethoxy, azido, —$NR^6SO_2R^5$, —$SO_2NR^5R^6$, —$NR^6C(O)R^5$, —$C(O)NR^5R^6$, —$NR^5R^6$, —$(CR^6R^7)_mOR^6$ wherein m is an integer from 1 to 5, —$OR^5$ and the substituents listed in the definition of $R^5$;
each $R^5$ is independently selected from H, $C_1$-$C_{10}$ alkyl, —$(CH_2)_t(C_6\text{-}C_{10}$aryl), and —$(CH_2)_t$(4-10 membered heterocyclic), wherein t is an integer from 0 to 5; said alkyl group optionally includes 1 or 2 hetero moieties selected from O, S and —$N(R^6)$— said aryl and heterocyclic $R^5$ groups are optionally fused to a $C_6$-$C_{10}$ aryl group, a $C_5$-$C_8$ saturated cyclic group, or a 4-10 membered heterocyclic group; and the foregoing $R^5$ substituents, except H, are optionally substituted by 1 to 3 substituents independently selected from nitro, trifluoromethyl, trifluoromethoxy, azido, —$NR^6C(O)R^7$, —$C(O)NR^6R^7$, —$NR^6R^7$, hydroxy, $C_1$-$C_6$ alkyl, and $C_1$-$C_6$ alkoxy;
each $R^6$ and $R^7$ is independently H or $C_1$-$C_6$ alkyl;
T, U and V are each independently selected from C (carbon), O (oxygen), N (nitrogen), and S (sulfur), and are included within $R^3$;
T, U, and V are immediately adjacent to one another; and
W is any non-hydrogen atom in $R^3$ that is not T, U, or V; or
(ii) hydrogen, halo, $C_1$-$C_{10}$ alkyl, $C_2$-$C_{10}$ alkenyl, $C_2$-$C_{10}$ alkynyl, nitro, trifluoromethyl, trifluoromethoxy, azido, —$OR^5$, —$NR^6C(O)OR^5$, —$NR^6SO_2R^5$, —$SO_2NR^5R^6$, —$NR^6C(O)R^5$, —$C(O)NR^5R^6$, —$NR^5R^6$, —$S(O)_jR^7$ wherein j is an integer ranging from 0 to 2, —$NR^5(CR^6R^7)_tOR^6$, —$(CH_2)_t(C_6\text{-}C_{10}$aryl), —$O(CH_2)_t(C_6\text{-}C_{10}$aryl), —$(CH_2)_t$(4-10 membered heterocyclic), and —$(CR^6R^7)_mOR^6$, wherein m is an integer from 1 to 5 and t is an integer from 0 to 5; said alkyl group optionally contains 1 or 2 hetero moieties selected from O, S and —$N(R^6)$—, wherein $R^5$, $R^6$ and $R^7$ are as defined above.

2. The compound according to claim 1, wherein each R represents mesityl.
3. The compound according to claim 1, wherein each R represents 2-ethylhexyl.
4. The compound according to claim 1, wherein each R represents a $C_1$-$C_{10}$ alkyl.
5. The compound according to claim 1, wherein each R represents a —$SO_2(CH_2)_t(C_6\text{-}C_{10}$aryl).
6. The compound according to claim 1, wherein each R represents a $C_6$-$C_{10}$ aryl.
7. A compound of the formula:

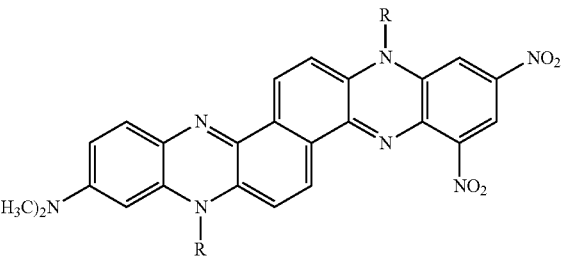

wherein each R represents a substituent selected from the group consisting of a $C_1$-$C_{10}$ alkyl, a —$SO_2(CH_2)_t(C_6\text{-}C_{10}$ aryl), and a $C_6$-$C_{10}$ aryl.

* * * * *